(12) United States Patent
Ito et al.

(10) Patent No.: US 6,730,508 B1
(45) Date of Patent: May 4, 2004

(54) PROTEIN PARTICIPATING IN THE ACTIVATION OF NITRILE HYDRATASE AND GENE ENCODING THE SAME

(75) Inventors: Kiyoshi Ito, Chiba-ken (JP); Miyuki Tsuruoka, Chiba-ken (JP); Tadashi Suzuki, Chiba-ken (JP); Seiya Nikumaru, Chiba-ken (JP); Takeshi Nakamura, Chiba-ken (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/265,383

(22) Filed: Mar. 10, 1999

(30) Foreign Application Priority Data

Mar. 16, 1998 (JP) ............................................ 10-065520

(51) Int. Cl.$^7$ ............................ C12N 1/21; C12N 1/19; C12N 15/31; C12N 15/63
(52) U.S. Cl. ............................... 435/252.3; 435/254.11; 435/320.1; 435/69.2; 536/23.7; 536/23.1
(58) Field of Search ............................... 536/23.1, 23.2, 536/23.7; 435/320.1, 252.3, 254.11, 69.2

(56) References Cited

U.S. PATENT DOCUMENTS 5,910,432 A * 6/1999 Ito et al. ...................... 435/129

FOREIGN PATENT DOCUMENTS

| EP | 0 790 310 | 8/1997 |
| JP | 8-56684 | 3/1996 |
| WO | WO 97/12964 | 4/1997 |

OTHER PUBLICATIONS

Kobayashi et al. "Metalloenzyme nitrile hydratase: structure, regulation, and application to biotechnology." Nature Biotechnology 16 (8):733–736, Aug. 1998.*

Hashimoto, Yoshihiro et al., "Nitrile Hydratase Gene from Rhodococcus sp. N–774 Requirement for Its Downstream Region for Efficient Expression." *Bioscience Biotechnology Biochemistry*, JP, Japan Soc. for Bioscience, Biotechnology and Agrochem, Tokyo, vol. 58, No. 10, Oct. 1994, pp. 1859–1865.

* cited by examiner

*Primary Examiner*—Gabriele Bugaisky
(74) *Attorney, Agent, or Firm*—Burns, Doane, Swecker & Mathis, LLP

(57) ABSTRACT

The invention provides a nitrile hydratase activation protein participating in activation of nitrile hydratase derived from *Pseudonocardia thermophila* JCM3095, and a gene sequence encoding the same. Further, the invention provides a recombinant plasmid containing the gene, a recombinant plasmid containing the gene and a nitrile hydratase gene, a transformant strain obtained through transformation with the recombinant plasmid, and a process for producing a corresponding amide compound from a nitrile compound using a culture solution and cells obtained by incubating the transformant strain and treated products of the cells.

16 Claims, 6 Drawing Sheets

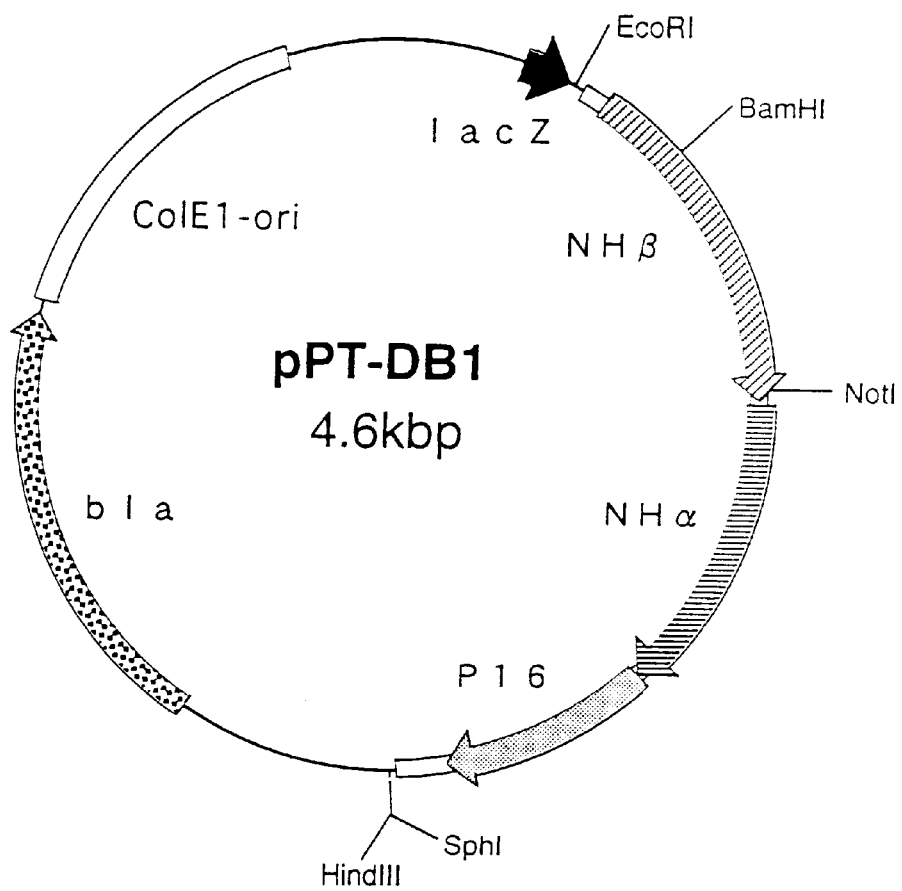
F I G. 1

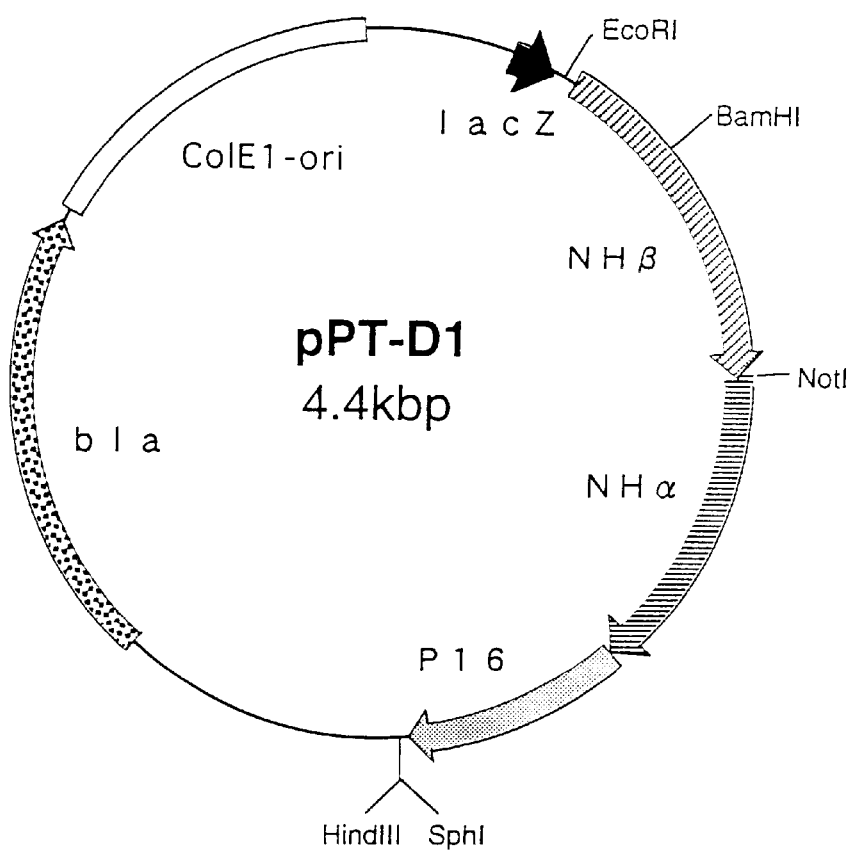
F I G. 2

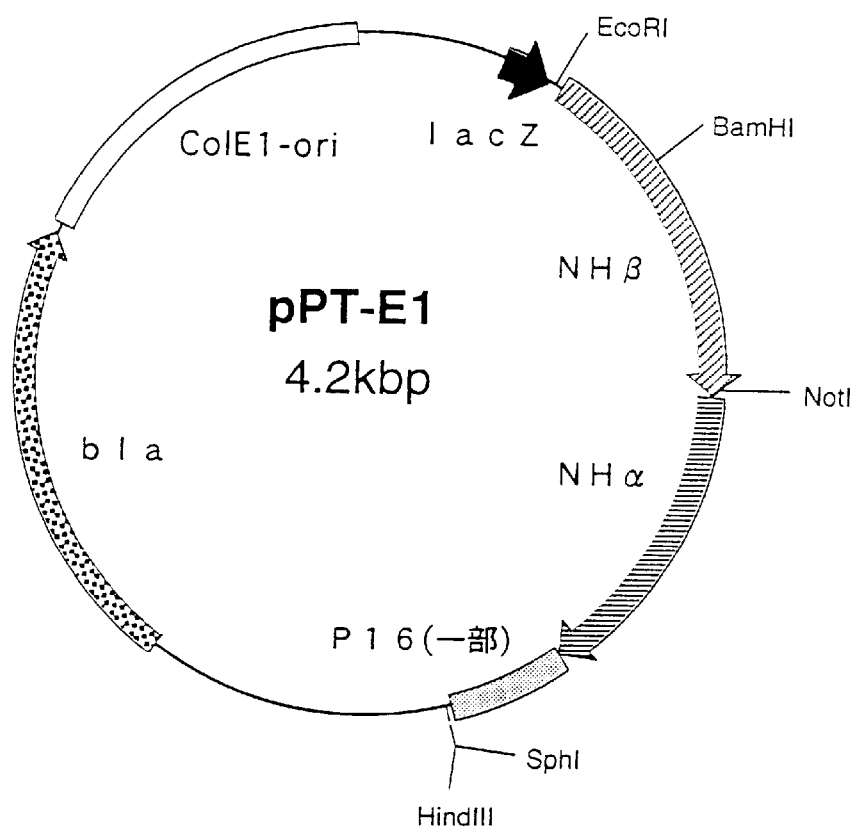
F I G. 3

```
                        SEQUENCE LISTING

<160> NUMBER OF SEQ ID NOS: 9

<210> SEQ ID NO 1
<211> LENGTH: 144
<212> TYPE: PRT
<213> ORGANISM: Pseudonocardia thermophila

<400> SEQUENCE: 1

Met Ser Ala Glu Ala Lys Val Arg Leu Lys His Cys Pro Thr Ala Glu
  1               5                  10                  15

Asp Arg Ala Ala Ala Asp Ala Leu Leu Ala Gln Leu Pro Gly Gly Asp
             20                  25                  30

Arg Ala Leu Asp Arg Gly Phe Asp Glu Pro Trp Gln Leu Arg Ala Phe
         35                  40                  45

Ala Leu Ala Val Ala Ala Cys Arg Ala Gly Arg Phe Glu Trp Lys Gln
     50                  55                  60

Leu Gln Gln Ala Leu Ile Ser Ser Ile Gly Glu Trp Glu Arg Thr His
 65                  70                  75                  80

Asp Leu Asp Asp Pro Ser Trp Ser Tyr Tyr Glu His Phe Val Ala Ala
                 85                  90                  95

Leu Glu Ser Val Leu Gly Glu Glu Gly Ile Val Glu Pro Glu Ala Leu
            100                 105                 110

Asp Glu Arg Thr Ala Glu Val Leu Ala Asn Pro Pro Asn Lys Asp His
        115                 120                 125

His Gly Pro His Leu Glu Pro Val Ala Val His Pro Ala Val Arg Ser
    130                 135                 140

<210> SEQ ID NO 2
<211> LENGTH: 1762
<212> TYPE: DNA
<213> ORGANISM: Pseudonocardia thermophila

<400> SEQUENCE: 2
tgagaggagc tccgcatgaa cggcgtgtac gacgtcggcg gcaccgatgg gctgggcccg     60
atcaaccggc ccgcggacga accggtcttc cgcgccgagt gggagaaggt cgcgttcgcg    120
```

-continued

```
atgttcccgg cgacgttccg ggccggcttc atgggcctgg acgagttccg gttcggcatc    180
gagcagatga acccggccga gtacctcgag tcgccgtact actggcactg gatccgcacc    240
tacatccacc acggcgtccg caccggcaag atcgatctcg aggagctgga gcgccgcacg    300
cagtactacc gggagaaccc cgacgccccg ctgcccgagc acgagcagaa gccggagttg    360
atcgagttcg tcaaccaggc cgtctacggc gggctgcccg caagccggga ggtcgaccga    420
ccgcccaagt tcaaggaggg cgacgtggtg cggttctcca ccgcgagccc gaagggccac    480
gcccggcgcg cgcggtacgt gcgcggcaag accgggacgg tggtcaagca ccacggcgcg    540
tacatctacc cggacaccgc cggcaacggc ctgggcgagt gccccgagca cctctacacc    600
gtccgcttca cggcccagga gctgtggggg ccggaagggg acccgaactc cagcgtctac    660
tacgactgct gggagcccta catcgagctc gtcgacacga aggcggccgc ggcatgaccg    720
agaacatcct gcgcaagtcg gacgaggaga tccagaagga gatcacggcg cgggtcaagg    780
ccctggagtc gatgctcatc gaacagggca tcctcaccac gtcgatgatc gaccggatgg    840
ccgagatcta cgagaacgag gtcggcccgc acctcggcgc gaaggtcgtc gtgaaggcct    900
ggaccgaccc ggagttcaag aagcgtctgc tcgccgacgg caccgaggcc tgcaaggagc    960
tcggcatcgg cggcctgcag ggcgaggaca tgatgtgggt ggagaacacc gacgaggtcc   1020
accacgtcgt cgtgtgcacg ctctgctcct gctacccgtg gccggtgctg gggctgccgc   1080
cgaactggtt caaggagccg cagtaccgct cccgcgtggt gcgtgagccc ggcagctgc    1140 tcaaggagga gttcggcttc gaggtcccgc cgagcaagga gatcaaggtc tgggactcca   1200
gctccgagat gcgcttcgtc gtcctcccgc agcgccccgc gggcaccgac gggtggagcg   1260
aggaggagct cgccaccctc gtcacccgcg agtcgatgat cggcgtcgaa ccggcgaagg   1320
cggtcgcgtg agcgccgagg cgaaggtccg cctgaagcac tgccccacgg ccgaggaccg   1380
ggcggcggcc gacgcgctgc tcgcgcagct gcccggcggc gaccgcgcgc tcgaccgcgg   1440
cttcgacgag ccgtgcagc tgcgggcgtt cgcgctggcg gtcgcggcgt gcagggcggg   1500
ccggttcgag tggaagcagc tgcagcaggc gctgatctcc tcgatcgggg agtgggagcg   1560
cacccacgat ctcgacgatc cgagctggtc ctactacgag cacttcgtcg ccgcgctgga   1620
atccgtgctc ggcgaggaag ggatcgtcga gccggaggcg ctggacgagc gcaccgcgga   1680
ggtcttggcc aacccgccga acaaggatca ccatggaccg catctggagc ccgtcgcggt   1740
ccacccggcc gtgcggtcct ga                                            1762
```

<210> SEQ ID NO 3
<211> LENGTH: 29
<212> TYPE: DNA
<213> ORGANISM: Pseudonocardia thermophila

<400> SEQUENCE: 3

```
cgaattctga gggagctcc gcatgaacg                                         29
```

<210> SEQ ID NO 4
<211> LENGTH: 28
<212> TYPE: DNA
<213> ORGANISM: Pseudonocardia thermophila

<400> SEQUENCE: 4

```
tgcatgctca ggaccgcacg gccgggtg                                         28
```

<210> SEQ ID NO 5

```
<211> LENGTH: 28
<212> TYPE: DNA
<213> ORGANISM: Pseudonocardia thermophila

<400> SEQUENCE: 5
tgcatgctca gatcgaggag atcagcgc                                      28

<210> SEQ ID NO 6
<211> LENGTH: 28
<212> TYPE: DNA
<213> ORGANISM: Pseudonocardia thermophila

<400> SEQUENCE: 6
tgcatgctca cgcgaccgcc ttcgccgg                                      28

<210> SEQ ID NO 7
<211> LENGTH: 45
<212> TYPE: DNA
<213> ORGANISM: Pseudonocardia thermophila

<400> SEQUENCE: 7
cgaattctga gaggagctcc gcgtgagcgc cgaggcgaag gtccg                   45

<210> SEQ ID NO 8
<211> LENGTH: 27
<212> TYPE: DNA
<213> ORGANISM: Pseudonocardia thermophila

<400> SEQUENCE: 8
tgcatgccat taatgcagct ggcacga                                       27

<210> SEQ ID NO 9
<211> LENGTH: 28
<212> TYPE: DNA
<213> ORGANISM: Pseudonocardia thermophila

<400> SEQUENCE: 9
taagctttca gatcgaggag atcagcgc                                      28
```

PROTEIN PARTICIPATING IN THE ACTIVATION OF NITRILE HYDRATASE AND GENE ENCODING THE SAME

DETAILED DESCRIPTION OF THE INVENTION

1. Technical Background of the Invention

The present invention relates to a protein participating in activation of nitrile hydratase derived from *Pseudonocardia thermophila* JCM3095 (hereinafter simply referred to as "*Pseudonocardia thermophila*") and a gene encoding the same. Further, the invention relates to a recombinant plasmid containing the gene, a recombinant plasmid containing the gene and a nitrile hydratase gene, a transformant strain obtained through transformation with the recombinant plasmid, and a process for producing a corresponding amide compound from a nitrile compound using the transformant strain, and a culture solution obtained by incubating the transformant treated products thereof.

2. Prior Art

In recent years, nitrile hydratase which is an enzyme having a nitrile hydration activity of converting a nitrile group of various compounds into an amide group through hydration, and a large number of microbial strains that produce this enzyme have been disclosed.

In order to industrially produce an amide compound from a nitrile compound using nitrile hydratase, it is important to reduce the production cost of the enzyme occupied in the production cost of the amide compound. More specifically, the content of the enzyme based on the unit weight of microbes has to be increased. In this respect, an approach to clone the gene of this enzyme has been studied to express the enzyme in a large amount by the method of the genetic engineering using the gene of the enzyme.

The present inventors discovered *Pseudonocardia thermophila* as a microbe having a nitrile hydratase activity (JP-A-8-56684). The inventors further isolated nitrile hydratase from the same strain, and identified that this enzyme composed of an α-subunit and a β-subunit. Still further, they isolated the nitrile hydratase gene from the same strain, clarified the amino acid sequence and the gene sequence thereof, and successfully produced a recombinant plasmid capable of expressing the gene *E. coli* (*Escherichia coli*) in a large amount and a transformant *E. coli* strain obtained through transformation with the same plasmid (European Patent Application Laid-Open No. 079310). By the way, with respect to *Pseudonocardia thermophila*, this strain is deposited as JCM3095 in International Patent Organism Depositary, National Institute of Advanced Industrial Science and Technology, AIST Tsukuba Central 6, 1-1, Higashi 1-chome, Tsukuba-shi, Ibaraki-ken, 305-8566, Japan, and freely allotted to any person on demand.

Problems that the Invention is to Solve

The invention is to provide a protein participating in activation of nitrile hydratase derived from *Pseudonocardia thermophila* described in European Patent Application Laid-Open No. 0790310 which was clarified by the detailed analysis of a recombinant plasmid (pPT-DB1) capable of expressing this enzyme in a large amount in *E.coli*, a gene encoding the same, a recombinant plasmid containing the gene, a recombinant plasmid containing the gene and a nitrile hydratase gene, a transformant strain obtained through transformation with the recombinant plasmid, and a process for producing a corresponding amide compound from a nitrile compound using the transformant strain, and a culture solution obtained through incubation of the transformant strain, or treated products thereof.

Means for Solving the Problems

The inventors have analyzed in detail the base sequence of the DNA fragment derived from *Pseudonocardia thermophila* in recombinant plasmid pPT-DB1 introduced in MT-10822 strain described in JP-A-9-275978. Consequently, they have acquired the following five findings. First, it has been found that the third open reading frame (hereinafter called "ORF3") different from nitrile hydratase structural genes (α- and βsubunit structural genes) is present in the DNA fragment in pPT-DB1 and ORF3 encodes a protein having a molecular weight of approximately 15,900. Second, they have produced plasmid pPT-D1 in which only the open reading frame of the α-subunit (hereinafter called "ORF2"), the open reading frame of the β-subunit (hereinafter called "ORF1") and ORF3 in pPT-DB1 are cloned, and have identified that transformant *E.coli* obtained through transformation with this plasmid has the nitrile hydratase activity. Third, they have constructed recombinant plasmid pPT-F1 having only ORF1 and ORF2 from pPT-DB1. As a result of measuring the nitrile hydratase activity of transformant *E.coli* obtained through transformation with this plasmid, the nitrile hydratase activity has not been detected from this *E.coli*. Meanwhile, the presence of polypeptide chains corresponding to the α- and β-subunits has been observed in the cell. Fourth, plasmid pPT-G1 in which only the ORF3 region is cloned has been produced from pPT-DB1, and it has been identified that the nitrile hydratase activity is not observed in transformant *E.coli* obtained through transformation with this plasmid. Fifth, plasmid pPT-H1 in which the region having lacZ promoter, ORF1 and ORF2 is amplified through PCR and the resulting amplified DNA fragment is re-cloned downstream of the 3'-terminus of ORF3 of pPT-G1 has been produced from pPT-F1. The nitrile hydratase activity of transformant *E.coli* obtained through transformation with this plasmid has been measured, and the nitrile hydratase activity has consequently been detected in this *E.coli*.

From these findings, the inventors have concluded that in order for *E.coli*, in which nitrile hydratase derived from *Pseudonocardia thermophila* has been introduced to exhibit the same activity, the presence of the ORF3 region is inevitable, and further that the presence of the translation product of ORF3 is inevitable in consideration of the second, third and fifth findings. Further, from the facts that the same enzyme is composed of the α-subunit and the β-subunit (European Patent Application Laid-Open No. 0790310) and that even when the minimum DNA fragment having the three open reading frames ORF1 to ORF3 is introduced in *E.coli*, recombinant *E.coli* exhibits the nitrile hydratase activity (second finding), it has been concluded that the translation product of ORF3 participates in activation of nitrile hydratase. That is, it has been concluded that ORF3 is a gene locus encoding a protein that participates in activation of nitrile hydratase derived from *Pseudonocardia thermophila*. Consequently, the invention has been completed.

That is, the invention is to provide a protein participating in activation of nitrile hydratase derived from *Pseudonocardia thermophila* and a gene encoding the same. Further, the invention is to provide a recombinant plasmid containing the gene, a recombinant plasmid containing the gene and a nitrile hydratase gene, a transformant strain obtained through transformation with the recombinant plasmid, and a process for producing a corresponding amide compound from a nitrile compound using the transformant strain, and a culture solution obtained through incubation of the transformant strain or treated products thereof.

BRIEF DESCRIPTION OF THE DRAWINGS

FIG. 1 is a restriction endonuclease cleavage point map of plasmid PT-DB1.

FIG. 2 is a restriction endonuclease cleavage point map of plasmid pPT-D1.

FIG. 3 is a restriction endonuclease cleavage point map of plasmid pPT-E1.

Figure 4:
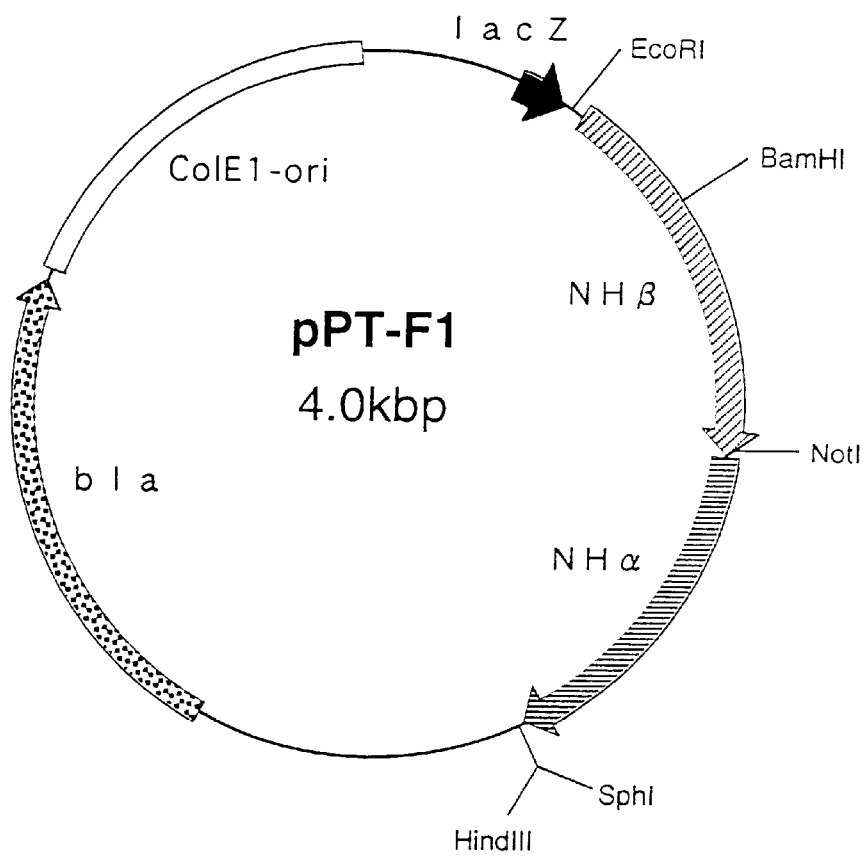
FIG. 4 is a restriction endonuclease cleavage point map of plasmid pPT-F1.

DESCRIPTION OF SYMBOLS bla: gene encoding β-lactamase
ColE1-Ori: ColE1-type replication initiation site
lacZ: promoter and operator regions of lactose operon derived from pUC18
NHα: gene encoding an α-subunit of nitrile hydratase derived from *Pseudonocardia thermophila*
NHβ: gene encoding a β-subunit of nitrile hydratase derived from *Pseudonocardia thermophila*
P16: gene encoding a protein that participates in activation of nitrile hydratase derived from *Pseudonocardia thermophila*
P16 (partial): partial region of a gene encoding a protein that participates in activation of nitrile hydratase derived from *Pseudonocardia thermophila*

MODE FOR CARRYING OUT THE INVENTION

The invention is described in detail below.

A protein that participates in activation of nitrile hydratase derived from *Pseudonocardia thermophila* JCM3095 (hereinafter simply referred to as "nitrile hydratase activation protein") in the invention is a protein of which the expression directly influences the activation of nitrile hydratase derived from *Pseudonocardia thermophila* as stated in Means For Solving the Problems and Examples to be described later.

As a typical example of the nitrile hydratase activation protein in the invention, a protein derived from *Pseudonocardia thermophila* can be mentioned. The progress of the molecular biology and the genetic engineering in recent years has made it possible and relatively easy to obtain a protein having the same function as the nitrile hydratase activation protein derived from *Pseudonocardia thermophila* from a microbial strain quite different from *Pseudonocardia thermophila* by directly referring to the molecular biological properties and the amino acid sequence of this nitrile hydratase activation protein. In view of such a state of the art, proteins that are derived from microbial strains other than *Pseudonocardia thermophila* but participate in activation of nitrile hydratase derived from *Pseudonocardia thermophila* are included in the invention. Preferable examples of such microbial strains include strains belonging to the genus Nocardia, Corynebacterium, Bacillus, thermophilic Bacillusi, Pseudomonas, Micrococcus, Rhodococcus typified by the species rhodochrous, Acinetobacter, Xanthobacter, Streptomyces, Rhizobium, Klebsiella, Enterobacter, Erwinia, Aeromonas, Citrobacter, Achromobacter, Agrobacterium or Pseudonocardia other than *Pseudonocardia thermophila* JCM3095 strain.

As a typical example of the nitrile hydratase activation protein in the invention, a protein composed of the amino acid sequence indicated in Sequence No. 1 of the sequence listing can be mentioned. Further, even when transcription and translation are conducted using a gene of the same base sequence as a template, a partial variant protein in which one or more amino acids in the vicinity of the N-terminus in the sequence table are deleted or one or more amino acids are newly added to the N-terminus though maintaining the predetermined function is sometimes produced through modification after translation with an enzyme in a host depending on a type of a host in which the gene is introduced, components or composition of nutrient medium used in incubation, an incubation temperature or pH. Still further, the progress of the recombinant DNA technology has made it possible one or more amino acids constituting a protein reletively easily to replace with other amino acid(s), to delete or excise one or more amino acids constituting a protein, or to insert an amino acid(s) into a protein, without substantially changing the function of the protein. In view of such a state of the art, the nitrile hydratase activation protein referred to in the invention includes not only a protein (1) having the amino acid sequence indicated in Sequence No. 1 of the sequence listing as such, but also partially variant protein having an amino acid sequence in which one or more amino acids are replaced with other amino acid(s), deleted or excised, or one or more amino acids are inserted, and also (2), and participating in activation of nitrile hydratase derived from *Pseudonocardia thermophila*.

That is, the typical example of the protein in the invention is a nitrile hydratase activation protein composed of the sequence of 144 amino acids indicated in Sequence No. 1 of the sequence listing. In addition, in the invention, a partially variant protein obtained by modifying a part of the amino acid sequence indicated in Sequence No. 1 of the sequence listing by replacing, deleting, excising or inserting is included in the invention so long as it participates in activation of the nitrile hydratase derived from *Pseudonocardia thermophila*.

With respect to the nitrile hydratase activation protein in the invention, a protein derived from *Pseudonocardia thermophila* and composed of the amino acid sequence indicated in Sequence No. 1 of the sequence listing can be mentioned as a typical example. Further, the progress of the genetic engineering in recent years has made it possible and relatively easy to obtain a protein having the same function as this protein from a microbial strain quite different from *Pseudonocardia thermophila* by directly referring to the amino acid sequence of the nitrile hydratase activation protein derived from *Pseudonocardia thermophila*. In view of such a state of the art, a protein derived from a microbial strain other than *Pseudonocardia thermophila* and having the amino acid sequence indicated in Sequence No. 1 of the sequence listing as such, or a protein (1) having an amino acid sequence in which one or more amino acids are replaced with other amino acids(s), deleted or excised, or one or more amino acids are inserted, and also participating in activation of nitrile hydratase derived from *Pseudonocardia thermophila* is included in the invention. Preferable examples of such a microbial strain include strains belonging to the genus Nocardia, Corynebacterium, Bacillus, thermophilic Bacillus, Pseudomonas, Micrococcus, Rhodococcus typified by the species rhodochrous, Acinetobacter, Xanthobacter, Streptomyces, Rhizobium, Klebsiella, Enterobacter, Erwinia, Aeromonas, Citrobacter, Achromobacter, Agrobacterium or Pseudonocardia other than *Pseudonocardia thermophila* JCM3095 strain.

The invention includes the sequence of the gene encoding the nitrile hydratase activation protein. The gene encoding the nitrile hydratase activation protein of the invention is not particularly limited so long as it is a gene encoding the nitrile hydratase activation protein of the invention.

In the invention, the base sequence encoding the sequence of 144 amino acids indicated in Sequence No. 1 of the sequence listing is included in the range of the gene encoding the nitrile hydratase activation protein of the invention. Further, in the invention, when the partially variant protein obtained by replacing, deleting or excising or inserting a part of the amino acid sequence indicated in Sequence No. 1 of the sequence listing or by inserting an amino acid(s) thereinto participates in the activation of nitrile hydratase derived from *Pseudonocardia thermophila*, the base sequence encoding the amino acid sequence of the partially variant protein is also included in the range of the gene encoding the nitrile hydratase activation protein of the invention.

With respect to the gene encoding the nitrile hydratase activation protein of the invention, the base sequence of 1328th to 1762nd bases indicated in Sequence No.2 of the sequence listing can be mentioned as the typical example. Further, the progress of the recombinant DNA technology has made it possible to replace the base sequence of DNA as a template in translation with another base sequence relatively easily without substantially changing the amino acid sequence of the protein. Still further, it has been possible that one or more amino acids constituting a protein are replaced with other amino acids(s), deleted or excised, or one or more amino acids are inserted thereinto, without substantially changing the function of the protein by subjecting the base sequence of DNA as a template in translation to replacing, deleting, excising or inserting treatment. In view of such a state of the art, the gene encoding the a nitrile hydratase activation protein in the invention includes not only the base sequence of 1328th to 1762nd bases indicated in Sequence No. 2 of the sequence listing as such, but also the partially variant sequence in which one or more bases of the DNA base sequence are replaced with other base(s), deleted, or excised, or one or more bases are inserted so long as it acts as a template of a protein participating in activation of nitrile hydratase derived from *Pseudonocardia thermophila*.

That is, the invention includes the gene encoding the nitrile hydratase activation protein and composed of the base sequence of 1328th to 1762nd bases indicated in Sequence No. 2 of the sequence listing. Further, the gene having the base sequence obtained by replacing, deleting, excising or inserting a part of the base sequence of 1328th to 1762nd bases indicated in Sequence No. 2 of the sequence listing, or obtained by inserting a base(s) into said base sequence is included in the gene encoding the nitrile hydratase activation protein of the invention so long as the protein encoded by the gene participates in activation of nitrile hydratase derived from *Pseudonocardia thermophila*.

The invention includes the construction of a recombinant plasmid having inserted therein the gene encoding the nitrile hydratase activation protein. Specifically, it is a plasmid in which the gene encoding the nitrile hydratase activation protein is inserted into a plasmid vector having a control region required for expression of the gene and a region required for autonomous replication.

The control region required for expression refers to a promoter sequence (including an operator sequence for controlling transcription), a ribosome binding sequence (SD sequence) and a transcription termination sequence. Specific examples of the promoter sequence include trp promoter of tryptophan operon and lac promoter of lactose operon derived from *E.coli*, $P_L$ promoter and $P_R$ promoter derived from λ phage, and gluconic acid synthetase promoter (gnt), alkali protease promoter (apr), neutral protease promoter (npr) and α-amylase promoter (amy) derived from *Bacillus subtilis*. Further, a sequence which is modified and designed independently, like tac promoter, can also be used. As a ribosome binding sequence, the inherent sequence of Pseudonocardia in the invention or the sequence derived from *E.coli* or *Basillus subtilis* can be mentioned. It is not particularly limited so long as it is a sequence which functions in a desired host such as *E.coli* or *Basillus subtilis*. For example, as a sequence complementary to a 3'-terminus region of 16S ribosomal RNA, a consensus sequence in which at least 4 bases are continued may be prepared through DNA synthesis and used. A transcription termination sequence is not necessarily required. A non-ρ-factor-dependent sequence, for example, lipoprotein terminator or trp operon terminator can be used. With respect to the order of the sequences in the recombinant plasmid of the control region, it is advisable that the promoter sequence, the ribosome binding sequence, the gene encoding the nitrile hydratase activation protein and the transcription termination sequence are arranged in this order from the 5'-terminus upstream.

Specific examples of the plasmid vector include pBR322, pUC18, Bluescript II SK (+), pKK223-3 and pSC101 having a region capable of autonomous replication in *E.coli*, and pUB110, pTZ4, pC194, p11, φ1 and φ105 having a region capable of autonomous replication in *Bacillus subtilis*. Further, examples of the plasmid vector capable of autonomous replication in two or more hosts include pHV14, TRp7, YEp7 and pBS7.

The invention includes the construction of a recombinant plasmid in which both the gene encoding the nitrile hydratase activation protein and the nitrile hydratase gene are inserted. That is, it is a recombinant plasmid obtained by inserting both genes into a plasmid vector containing a control region(s) required for expression of both genes and a region(s) required for autonomous replication. It is a recombinant plasmid which, when introduced into any host, allows production and activation of the enzyme. Specifically, the above-mentioned plasmid vector containing the control region required for expression and the region required for autonomous replication may be selected. Further, the gene encoding the nitrile hydratase activation protein, and the aα-subunit gene and the β-subunit gene of nitrile hydratase may be expressed as independent cistrons with such a control region(s) or as a polycistron with a common control region.

As a typical example of the nitrile hydratase gene of the invention, the nitrile hydratase gene derived from *Pseudonocardia thermophila* can be mentioned. Specifically, the gene encoding the α-subunit represented by the base sequence of 714th to 1331st bases indicated in Sequence No. 2 of the sequence listing and the gene encoding the β-subunit represented by the base sequence of 16th to 717th bases indicated in Sequence No. 2 of the sequence listing are mentioned. That is, it is basically nitrile hydratase in which the α-subunit is composed of the base sequence of 618 bases and the β-subunit is composed of the base sequence of 702 bases. The progress of the recombinant DNA technology has made it possible that the base sequence of DNA as a template in translation is replaced with another base sequence relatively easily without substantially changing the amino acid sequence of the enzyme, or that one or more amino acids constituting the enzyme are replaced with other amino acids, deleted, or excised, or one or more amino acids are inserted, without substantially changing the activity of the enzyme by replacing, deleting or excising the base sequence of DNA as a template in translation or by inserting a base(s) into the base sequence. In view of such a state of the art, the nitrile hydratase gene derived from *Pseudonocardia thermophila* referred to in the invention includes not only the gene having the α-subunit represented by the base sequence of 714th to 1331st bases indicated in Sequence No. 2 of the sequence listing and the β-subunit represented by the base sequence of 16th to 717th bases indicated in Sequence No. 2 of the sequence listing as such, but also the gene of the partially variant sequence in which one or more bases of the DNA base sequence are replaced with other bases, deleted, or excised, or one or more bases are inserted thereinto, so long as it can acts as a template of the protein having the nitrile hydratase activity.

Specifically, as described in European Patent Application Laid-Open No. 0790310, a nitrile hydratase gene having as a constituent an α-subunit gene represented by the base sequence obtained by replacing with other base sequence(s) one or more of base sequences of 729th to 731st bases, 768th to 770th bases, 825th to 827th bases, 942nd to 944th bases, 981st to 983rd bases, 1017th to 1019th bases, 1029th to 1031st bases, 1089th to 1091st bases, 1101st to 1103rd bases, 1137th to 1139th bases, 1149th to 1151st bases, 1272nd to 1274th bases, 1293rd to 1295th bases and 1320th to 1322nd bases indicated in Sequence No. 2 of the sequence listing, can be mentioned.

That is, the invention includes the gene encoding nitrile hydratase having as a constituent the a α-subunit obtained by replacing with other amino acid(s) one or more of 6th, 19th, 38th, 77th, 90th, 102nd, 106th, 126th, 130th, 142nd, 146th, 187th, 194th and 203rd amino acids.

Likewise, a nitrile hydratase gene having as a constituent the β-subunit gene represented by the base sequence obtained by replacing with other base sequence(s) one or more of base sequences of 73rd to 75th bases, 76th to 78th bases, 337th to 339th bases, 613th to 615th bases and 649th to 651st bases indicated in Sequence No. 2 of the sequence listing can be mentioned.

That is, the invention includes the gene encoding nitrile hydratase and having as a constituent the β-subunit obtained by replacing with other amino acid(s) one or more amino acid(s) of 20th, 21st, 108th, 200th and 212th amino acids of the β-subunit.

The nitrile hydratase gene in the invention is not particularly limited to the gene derived from *Pseudonocardia thermophila*, and it also includes the nitrile hydratase gene derived form other microbial strains so long as they are activated with the nitrile hydratase activation protein of the invention. Preferable examples of such microbial strains include strains belonging to the genus Nocardia, Corynebacterium, Bacillus, thermophilic Pseudomonoas, Micrococcus, Rhodococcus typified by the species rhodochrous, Acinetobacter, Xanthobacter, Streptomyces, Rhizobium, Klebsiella, Enterobacter, Erwinia, Aeromonas, Citrobacter, Achromobacter, Agrobacterium or Pseudonocardia other than *Pseudonocardia thermophila* JCM3095 strain.

The invention includes the procurement of the transformant by introducing the recombinant plasmid into an optional microbial host. At this time, a recombinant plasmid in which the gene encoding the nitrile hydratase activation protein and the α-subunit gene and the β-subunit gene of nitrile hydratase are present in the same plasmid vector may be used, or a plurality of recombinant plasmids in which the respective genes are present in independent plasmid vectors may be introduced simultaneously. Further, as the optional host here referred to, *E.coli* is mentioned as a typical example. However, it is not particularly limited to *E.coli*, and also includes strains belonging to the genus Bacillus, such as *Bacillus subtilis*, and other microbial strains such as yeast and actinomycetes. An example is, MT-10822 (this strain was deposited under the Japanese Rule on Feb. 7, 1996 and allotted No. FERM P-15426 in the National Institute of Bioscience and Human-Technology of the Agency of Industrial Science and Technology of the Ministry of International Trade and Industry, and then was transferred to the International deposit under the Budapest Treaty and allotted No. FERM BP-5785 in said depositary on Jan. 10, 1997; the address of the depositary is 1-3, Higashi 1 chome, Tsukuba-shi, Ibaraki-ken, Japan.).

With respect to a method of constructing the recombinant plasmid of the invention by inserting the gene encoding the nitrile hydratase activation protein of the invention and/or the nitrile hydratase gene derived from *Pseudonocardia thermophila* into the plasmid vector having the region required for the expression of a foreign gene(s), the recombinant plasmid may be transformed into a desired host by referring to a general method which is known in the field of the genetic engineering as described in "Molecular Cloning 2nd Edition" (T. Maniatis et al.; Cold Spring Harbor Laboratory Press, 1989).

The invention includes a process for producing a corresponding amide compound from a nitrile compound, which comprises introducing a gene encoding a nitrile hydratase activation protein and a nitrile hydratase gene into a host simultaneously, incubating the resulting transformant in a general nutrient medium to produce the enzyme, preparing a transformant strain producing this enzyme, a culture solution of the transformant strain, the transformant cells obtained from the culture solution of the transformant strain or treated product of the transformant cells, and contacting any one of them with a nitrile compound in an aqueous medium. The transformant strain may be prepared by using a general method known in the field of the molecular biology, the biological engineering and the genetic engineering. For example, it is advisable that the transformant strain is inoculated in an ordinary liquid medium such as an LB medium or an M9 medium (preferably, Fe ions and Co ions are present in an amount of 0.1 $\mu$g/mL or more in such a medium component) and grown at an appropriate incubation temperature (generally between 20° C. and 50° C.). Further, the culture solution itself, the transformant cells obtained by separation and recovery :from the culture solution through centrifugation and the treated product of the transformant cells can also be used. The treated product of the transformant cells here referred to includes extract of the cells, the milled cells product obtained by separating and purifying the nitrile hydratase active fraction of the extract or the milled cells, or the immobilized product obtained by immobilizing the transformant cells or the extract, the milled cells or the said product using an appropriate carrier. The nitrile compound from which to produce the corresponding amide compound is not particularly limited so long as it can act as a substrate for the nitrile hydratase of the invention. Preferable typical examples thereof include nitrile compounds such as acetonitrile, propionitrile, acrylonitrile, methacrylonitrile, n-butyronitrile, isobutyronitrile, crotononitrile, (α-hydroxyisobutyronitrile, ethylenecyanohydrin, fumaronitrile, malononitrile, benzonitrile, mandelonitrile, cyanopyrazine and 3-cyanopyridine. The concentration of the nitrile compound in the aqueous medium is not particularly limited. The reaction temperature is not particularly limited either. It is preferably in such a temperature range that nitrile hydratase is not deactivated, more preferably between 0° C. and 50° C.

EXAMPLES

The invention is illustrated more specifically by referring to the following Examples. However, the invention is not limited thereto.

In the HPLC analysis in Examples and Comparative Examples, Finepak SIL C18-5 (250×4.6 mm (diameter)) supplied by Nippon Bunko was used as a column, and a 10 mM phosphate aqueous solution containing 4% by volume of acetonitrile as an eluent. Further, acrylamide, acrylonitrile and acrylic acid were detected by absorbance at 210 nm.

Example 1
Analysis of an insertion fragment of MT-10822 strain (1)

One hundred milliliters of a medium having the following formulation was charged into a 500-milliliter three-necked flask fitted with a baffle, and was autoclaved at 121° C. for 20 minutes. Ampicillin was added to this medium such that the final concentration reached 100 μg/mL, and one loopful of MT-10822 strain (FERM BP-5785) was inoculated therein, and incubated at 37° and 130 rpm for 16 hours. Only the cells were separated from the culture solution through centrifugation at 15,000 G for 15 minutes. Subsequently, the cells were resuspended in 50 mL of a physiological saline solution, and the wet cells were then obtained through recentrifugation.

| Medium formulation: | |
|---|---|
| yeast extract | 5.0 g/liter |
| polypeptone | 10.0 g/liter |
| NaCl | 5.0 g/liter |
| cobalt chloride.6-hydrate | 10.0 mg/liter |
| ferrous sulfate.7-hydrate | 40.0 mg/liter |
| pH 7.5 | |

A plasmid DNA of pPT-DB1 (FIG. 1) was prepared from the wet cells by the alkali SDS extraction method. The whole base sequence of the insertion fragment was determined by the primer extension method using a sequencing kit and an autosequencer 373 A supplied by ABI. Consequently, the open reading frames (called ORF1, ORF2 and ORF3 respectively) having base sequences of 705 bp, 621 bp and 435 bp were observed in the insertion fragment from the 5'-terminus side in this order. Further, the transcription directions of these frames were completely consistent. The four bases at the side closest to the 3'-terminus in ORF1 including the translation termination codon overlapped with the four bases at the side closest to the 5'-terminus in ORF2. Likewise, the four bases at the side closest to the 3'-terminus in ORF2 including the translation termination codon overlapped with the four bases at the side closest to the 5'-terminus in ORF3. As already described in JP-A-9-275978, ORF1 is a β-subunit gene of nitrile hydratase, and ORF2 an α-subunit gene thereof.

Then, for re-cloning of the overall region from ORF1 to ORF3, PCR was conducted using pPT-DB1 plasmid DNA as a template.

A procedure comprising thermal denaturation at 98° C. for 15 seconds, annealing at 55° C. for 30 seconds and an elongation reaction at 72° C. for 120 seconds was repeated at 25 cycles in a system, in a total amount of 100 μL, containing 100 pmols of the primer indicated in Sequence No. 3 of the sequence listing, 100 pmols of the primer indicated in Sequence No. 4 of the sequence listing and 5 U of Taq DNA polymerase using 1 μg of pPT-DB1 plasmid DNA as a template. The analysis of the amplified DNA product was conducted through agarose electrophoresis (using Type VII low-melting agarose supplied by Sigma; agarose concentration 0.8% by weight) using 10 μL of the PCR reaction solution. Consequently, the presence of the amplified DNA product of approximately 1.8 kbp was identified. Subsequently, only the DNA fragment of approximately 1.8 kbp was cut from the agarose gel. Approximately 0.1 g of the agarose portion were finely divided, and suspended in 1 mL of a TE solution. The suspension was maintained at 55° C. for 1 hour to completely melt agarose. This melt was subjected to extraction with phenol and chloroform, and ethanol precipitation. First, 1 mL of a phenol solution saturated with TE (10 mM Tris hydrochloride aqueous solution containing 1 mM EDTA·2Na; pH 8.0) was added thereto, and the mixture was gently, stirred. The aqueous phase and the organic phase were separated through centrifugation at 3,000 rpm for 10 minutes, and the aqueous phase was alone collected. This procedure was repeated three times. Then, to the resulting aqueous phase were added 0.4 mL of the TE-saturated phenol solution and 0.4 mL of chloroform. The mixture was gently restirred. Subsequently, the aqueous phase and the organic phase were reseparated through centrifugation at 3,000 rpm for 10 minutes, and the aqueous phase alone was recollected. To this aqueous phase was added 0.8 mL of chloroform. The mixture was gently restirred. Then, the aqueous phase and the organic phase were reseparated through centrifugation at 3,000 rpm for 10 minutes, and the aqueous phase alone was collected. To this aqueous phase was added 80 μL of a TE solution containing 1.1 M NaCl and 1.7 mL of ethanol. The mixture was allowed to stand at −80° C. for 30 minutes. Thereafter, the precipitate of the DNA fragment was recovered through centrifugation at 4° C. and 15,000 rpm for 20 minutes. The DNA fragment was dried with air, and then finally dissolved in 10 μL of TE. The amplified DNA fragment of approximately 1.8 kbp purified was cut from with restriction endonucleases EcoRI and SphI. This restriction endonucrease-treated solution was subjected to the above-mentioned extraction with phenol and chloroform, and ethanol precipitation to repurify the DNA fragment. Finally, this fragment was dissolved in 10 μL of TE. Likewise, pUC18 vector was cleaved with EcoRI and SphI, at the sole restriction endonuclease sites in the vector. The agarose gel electrophoresis (using Type VII low-melting agarose supplied by Sigma; agarose concentration 0.7%) was conducted, and only the DNA fragment of approximately 2.7 kbp was cut from the agarose gel. The agarose portion (approximately 0.1 g) cut was finely divided, and suspended in 1 mL of the TE solution. The suspension was then maintained at 55° C. for 1 hour to completely melt the agarose. This melt was subjected to the above-mentioned extraction with phenol and chloroform, and ethanol precipitation to purify the DNA fragment. Finally, this fragment was dissolved in 10 μL of TE. The thus-obtained amplified DNA product was ligated with the pUC18 fragment using a DNA ligation kit (supplied by Takara Shuzo) to construct plasmid pPT-D1 (FIG. 2). Further, the whole base sequence of the insertion fragment between the EcoRI site and the SphI site of pPT-D1 constructed is indicated in Sequence No. 2 of the sequence listing.

pPT-D1 was introduced into HB101 strain using competent cells of E.coli HB101 supplied by Toyobo Co., Ltd. to obtain transformant strain No. 1. An LB liquid medium having the above-mentioned formulation was charged into a 500-milliliter three-necked flask fitted with a baffle, and autoclaved at 121° C. for 20 minutes. Ampicillin was added to this medium such that the final concentration reached 100 μg/mL, and one loopful of the resulting transformant strain No. 1 was inoculated therein, and incubated at 37° C. and 130 rpm for approximately 20 hours. Only the cells were separated from the culture solution through centrifugation at 5,000 G for 15 minutes. Subsequently, the cells were resuspended in 50 mL of a physiological saline solution, and the wet cells were then obtained through recentrigation. One hundred milligrams of the wet cells was suspended in 200 mL of a 50 mM potassium phosphate aqueous solution (pH 7.0), and 10 mL of acrylonitrile were added to this suspension. The mixture was reacted at 10° C. for 1 hour while being gently stirred. After the completion of the reaction, the reaction solution was analyzed through HPLC as in Example 1. Then, only acrylamide was present in the reaction solution, and acrylonitrile and acrylic acid were not observed therein. That is, the conversion and the selectivity were 100%.

Comparative Example 1

Analysis of an insertion fragment of MT-10822 strain (2)
For re-cloning from ORF1 region to the upper half region of ORF3, PCR was conducted using pPT-DB1 plasmid DNA as a template.

A procedure comprising thermal denaturation at 98° C. for 15 seconds, annealing at 55° C. for 30 seconds and an elongation reaction at 72° C. for 120 seconds was repeated at 25 cycles in a system, in a total amount of 100 μL, containing 100 pmols of the primer indicated in Sequence No. 3 of the sequence table, 100 pmols of the primer indicated in Sequence No. 5 of the sequence listing and 5 U of Taq DNA polymerase using 1 μg of pPT-DB1 plasmid DNA prepared in Example 1 as a template. The analysis of the amplified DNA product was conducted through agarose electrophoresis (using Type VII low-melting agarose supplied by Sigma; agarose concentration 0.9% by weight) using 10 μL of the PCR reaction solution. Consequently, the presence of the amplified DNA product of approximately 1.6 kbp was identified. Subsequently, only the DNA fragment of approximately 1.6 kbp was cut from the agarose gel. Approximately 0.1 g of the agarose portion were finely divided, and suspended in 1 mL of a TE solution. The suspension was maintained at 55° C. for 1 hour to completely melt agarose. This melt was subjected to extraction with phenol and chloroform, and ethanol precipitation as in Example 1 to purify the amplified DNA fragment. The amplified DNA fragment of approximately 1.6 kbp purified was cleaved with restriction endonucleases EcoRI and SphI. The restriction endonuclease-treated solution was then subjected to extraction with phenol and chloroform, and ethanol precipitation as in Example 1 to repurify the DNA fragment, and this was finally dissolved in 10 μL of TE. The resulting amplified DNA product and the pUC18 EcoRI-SphI fragment of approximately 2.7 kbp produced in Example 1 were ligated using a DNA ligation kit (supplied by Takara Shuzo) to construct plasmid pPT-E1 (FIG. 3).

pPT-E1 was introduced into HB101 strain using competent cells of E.coli HB101 supplied by Toyobo Co., Ltd. to obtain transformant strain No. 2. An LB liquid medium having the same formulation as in Example 1 was charged into a 500-milliliter three-necked flask fitted with a baffle, and autoclaved at 121° C. for 20 minutes. Ampicillin was added to this medium such that the final concentration reached 100 μg/mL, and one loopful of the resulting transformant strain No. 2 was then inoculated therein, and incubated at 37° and 130 rpm for approximately 20 hours. Only the cells were separated from the culture solution through centrifugation at 5,000 G for 15minutes. Subsequently, the cells were resuspended in 50 mL of a physiological saline solution, and the wet cells were then obtained through recentrifugation. One hundred milligrams of the wet cells were suspended in 200 mL of a 50 mM potassium phosphate aqueous solution (pH 7.0), and 10 mL of acrylonitrile were added to this suspension. The mixture was reacted at 10° C. for 1 hour while being gently stirred. After the completion of the reaction, the reaction solution was analyzed through HPLC as in Example 1. Then, no acrylamide was observed in the reaction solution, and only unreacted acrylonitrile was observed therein. Further, no acrylic acid was observed therein. That is, the conversion and the selectivity were 0%.

Meanwhile, the presence of polypeptide chains corresponding to the α- and β-subunits of Pseudonocardia thermophila was observed in the cells separated from the culture solution.

Comparative Example 2

Analysis of an insertion fragment of MT-10822 strain (3)
For re-cloning of the overall region from ORF1 to ORF2, PCR was conducted using pPT-DB1 plasmid DNA as a template.

A procedure comprising thermal denaturation at 98° C. for 15 seconds, annealing at 55° C. for 30 seconds and an elongation reaction at 72° C. for 120 seconds was repeated at 25 cycles in a system, in a total amount of 100 μL containing 100 pmols of the primer indicated in Sequence No. 3 of the sequence listing, 3100 pmols of the primer indicated in Sequence No. 6 of the sequence listing and 5 U of Taq DNA polymerase using 1 μg of pPT-DB1 plasmid DNA prepared in Example 1 as a template. The analysis of the amplified DNA product was conducted through agarose electrophoresis (using Type VII low-melting agarose supplied by Sigma; agarose concentration 0.9% by weight) using 10 μL of the PCR reaction solution. Consequently, the presence of the amplified DNA product of approximately 1.3 kbp was identified. Subsequently, only the DNA fragment of approximately 1.3 kbp was cut from the agarose gel. Approximately 0.1 g of the agarose portion was finely divided, and suspended in 1 mL of a TE solution. The suspension was maintained at 55° C. for 1 hour to completely melt agarose. This melt was subjected to extraction with phenol and chloroform, and ethanol precipitation as in Example 1 to purify the amplified DNA fragment. The amplified DNA fragment of approximately 1.3 kbp was cut from with restriction endonucleases EcoRI and SphI. The restriction endonuclease-treated solution was then subjected to extraction with phenol and chloroform, and ethanol precipitation as in Example 1 to repurify the DNA fragment, and this was finally dissolved in 10 μL of TE. The resulting amplified DNA product and the pUC18 EcoRI-SphI fragment of approximately 2.7 kbp produced in Example 1 were ligated using a DNA ligation kit (supplied by Takara Shuzo) to construct plasmid pPT-F1 (FIG. 4).

pPT-F1 was introduced into HB101 strain using competent cells of E.coli HB101 supplied by Toyobo Co., Ltd. to obtain transformant strain No. 3. An LB liquid medium having the same formulation as in Example 1 was charged into a 500-milliliter three-necked flask fitted with a baffle, and autoclaved at 121° C. for 20 minutes. Ampicillin was added to this medium such that the final concentration reached 100 µg/mL, and one loopful of the resulting transformant strain No. 3 was then inoculated therein, and incubated at 37° C. and 130 rpm for approximately 20 hours. Only the cells were separated from the culture solution through centrifugation at 5,000 G for 15 minutes. Subsequently, the cells were resuspended in 50 mL of a physiological saline solution, and the wet cells were then obtained through recentrifugation. One hundred milligrams of the wet cells were suspended in 200 mL of a 50 mM potassium phosphate aqueous solution (pH 7.0), and 10 mL of acrylonitrile was added to this suspension. The mixture was reacted at 10° C. for 1 hour while being gently stirred. After the completion of the reaction, the reaction solution was analyzed through HPLC as in Example 1. Then, no acrylamide was observed in the reaction solution, and only unreacted acrylonitrile was observed therein. Further, no acrylic acid was observed therein. That is, the conversion and the selectivity were 0%.

Meanwhile, the presence of polypeptide chains corresponding to the α- and β-subunits of nitrile hydratase derived from *Pseudonocardia thermophila* was observed in the cells separated from the culture solution.

Comparative Example 3
Analysis of an insertion fragment of MT-10822 strain (4)
For re-cloning of the overall region of ORF3, PCR was conducted using pPT-DB1 plasmid DNA as a template.

Figure 5:
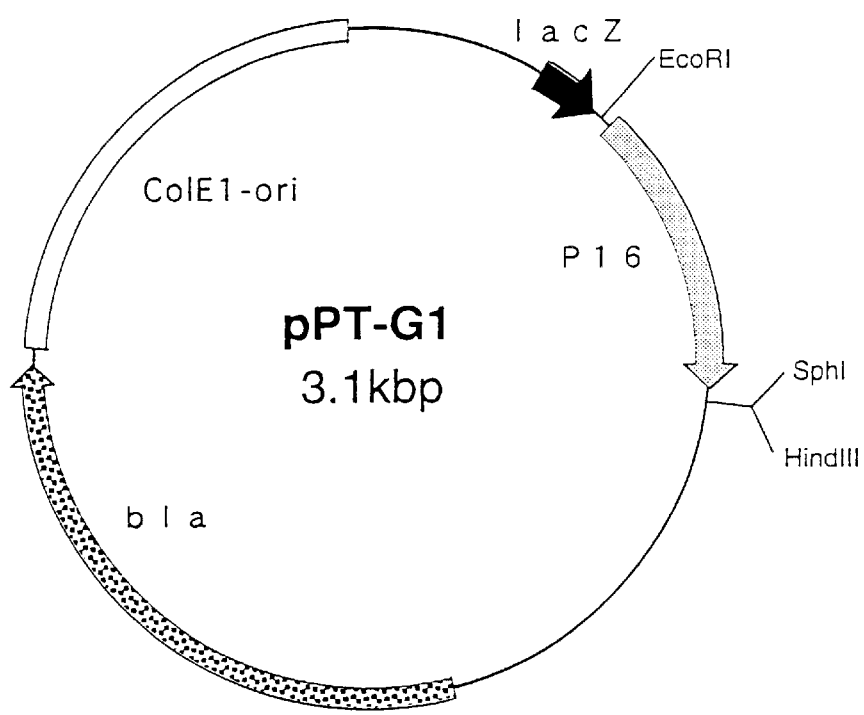
FIG. 5 is a restriction endonuclease cleavage point map of plasmid pPT-G1.

A procedure comprising thermal denaturation at 98° C. for 15 seconds, annealing at 55° C. for 30 seconds and an elongation reaction at 72° C. for 120 seconds was repeated at 25 cycles in a system, in a total amount of 100 µL containing 100 pmols of the primer indicated in Sequence No. 7 of the sequence listing, 100 pmols of the primer indicated in Sequence No. 4 of the sequence listing and 5 U of Taq DNA polymerase using 1 µg of pPT-DB1 plasmid DNA prepared in Example 1 as a template. The analysis of the amplified DNA product was conducted through agarose electrophoresis (using Type VII low-melting agarose supplied by Sigma; agarose concentration 1.2% by weight) using 10 µl of the PCR reaction solution. Consequently, the presence of the amplified DNA product of approximately 450 bp was identified. Subsequently, only the DNA fragment of approximately 450 bp purified was cut from the agarose gel. Approximately 0.1 g of the agarose portion was finely divided, and suspended in 1 mL of a TE solution. The suspension was maintained at 55° C. for 1 hour to completely melt agarose. This melt was subjected to extraction with phenol and chloroform, and ethanol precipitation as in Example 1 to purify the amplified DNA fragment. The amplified DNA fragment of approximately 450 bp was cleaved with restriction endonucleases EcoRI and SphI. The restriction endonuclease-treated solution was then subjected to extraction with phenol and chloroform, and ethanol precipitation as in Example 1 to repurify the DNA fragment, and it was finally dissolved in 10 µL of TE. The resulting amplified DNA product and the pUC18 EcoRI-SphI fragment of approximately 2.7 kbp produced in Example 1 were ligated using a DNA ligation kit (supplied by Takara Shuzo) to construct plasmid pPT-G1 (FIG. 5).

pPT-G1 was introduced into HB101 strain using competent cells of *E.coli* HB101 supplied by Toyobo Co., Ltd. to obtain transformant strain No. 4. An LB liquid medium having the same formulation as in Example 1 was charged into a 500-milliliter three-necked flask fitted with a baffle, and autoclaved at 121° C. for 20 minutes. Ampicillin was added to this medium such that the final concentration reached 100 µg/mL, and one loopful of the resulting transformant strain No. 4 was inoculated therein, and incubated at 37° C. and 130 rpm for approximately 20 hours. Only the cells were separated from the culture solution through centrifugation at 5,000 G for 15 minutes. Subsequently, the cells were resuspended in 50 mL of a physiological saline solution, and the wet cells were then obtained through recentrifugation. One hundred milligrams of the wet cells was suspended in 200 mL of a 50 mM potassium phosphate aqueous solution (pH 7.0), and 10 mL of acrylonitrile was added to this suspension. The mixture was reacted at 10° C. for 1 hour while being gently stirred. After the completion of the reaction, the reaction solution was analyzed through HPLC as in Example 1. Then, no acrylamide was observed in the reaction solution, and only unreacted acrylonitrile was observed therein. Further, no acrylic acid was observed therein. That is, the conversion and the selectivity were 0%.

Example 2
Analysis of an insertion fragment of MT-10822 strain (5)
A region containing lacZ promoter, ORF2 of the β-subunit and ORF1 of the a α-subunit in pPT-F1 produced in Comparative Example 2 was cloned in the 3'-terminus side of the ORF3 region of pPT-G1 plasmid.

Figure 6:
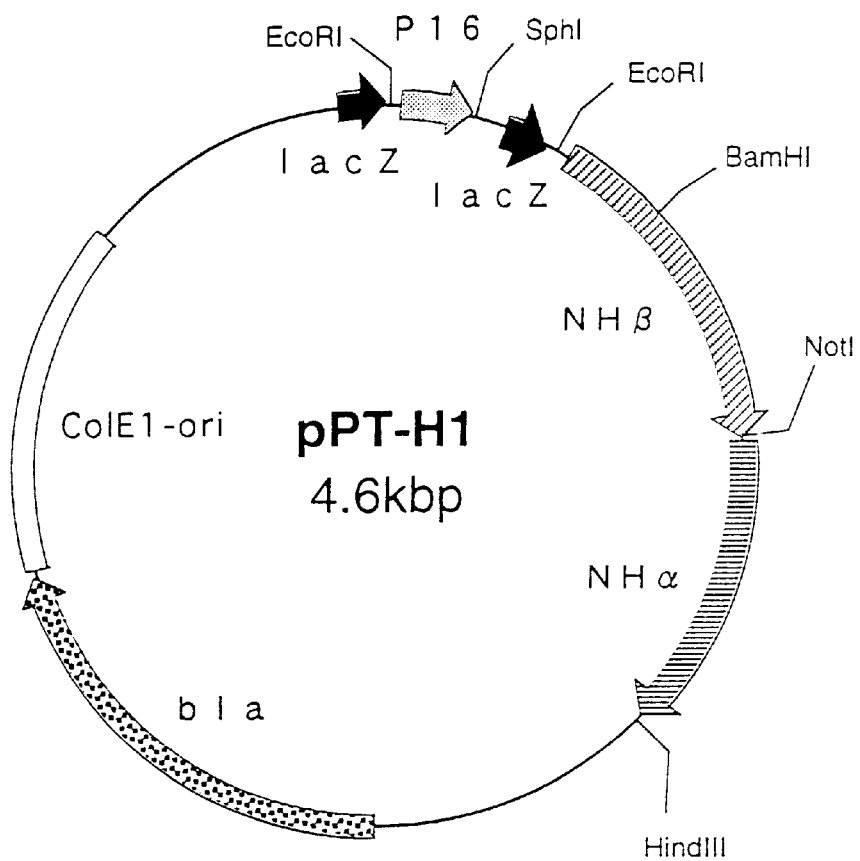
FIG. 6 is a restriction endonuclease cleavage point map of plasmid pPT-H1.

A procedure comprising thermal denaturation at 98° C. for 15 seconds, annealing at 55° C. for 30 seconds and an elongation reaction at 72° C. for 120 seconds was repeated at 25 cycles in a system in a total amount of 100 µL containing 100 pmols of the primer indicated in Sequence No. 8 of the sequence listing, 100 pmols of the primer indicated in Sequence No. 9 of the sequence listing and 5 U of Taq DNA polymerase using 1 µg of pPT-F1 plasmid DNA prepared in Comparative Example 1 as a template. The analysis of the amplified DNA product was conducted through agarose electrophoresis (using Type VII low-melting agarose supplied by Sigma; agarose concentration 0.8% by weight) using 10 µL of the PCR reaction solution. Consequently, the presence of the amplified DNA product of approximately 2.0 kbp was identified. Subsequently, only the DNA fragment of approximately 2.0 kbp was cut from the agarose gel. Approximately 0.1 g of the agarose portion was finely divided, and suspended in 1 mL of a TE solution. The suspension was maintained at 55° C. for 1 hour to completely melt agarose. This melt was subjected to extraction with phenol and chloroform, and ethanol precipitation as in Example 1 to purify the amplified DNA fragment. The amplified DNA fragment of approximately 2.0 kbp was cleaved with restriction endonucleases SphI and HindIII. The restriction endonuclease-treated solution was then subjected to extraction with phenol and chloroform, and ethanol precipitation as in Example 1 to repurify the DNA fragment, and it was finally dissolved in 10 µL of TE. Likewise, the same plasmid was cleaved with SphI and HindIII, at the sole restriction endonuclease sites of pPT-G1 plasmid. The agarose gel electrophoresis (using Type VII low-melting agarose supplied by Sigma; agarose concentration 0.7%) was conducted, and only the DNA fragment of approximately 3.1 kbp was cut from the agarose gel. Approximately 0.1 g of the agarose portion cut was finely divided, and suspended in 1 mL of a TE solution. The suspension was then maintained at 55° C. for 1 hour to completely melt the agarose. This melt was subjected to extraction with phenol and chloroform, and ethanol precipitation as in Example 1 to purify the DNA fragment, and it was finally dissolved in 10 µL of TE. The resulting amplified DNA product and the pPT-G1 SphI-HindIII fragment were ligated using a DNA ligation kit (supplied by Takara Shuzo) to construct plasmid pPT-H1 (FIG. 6).

pPT-H1 was introduced into HB101 strain using competent cells of *E.coli* HB101 supplied by Toyobo Co., Ltd. to obtain transformant strain No. 5. An LB liquid medium having the above-mentioned formulation was charged into a 500-milliliter three-necked flask fitted with a baffle, and autoclaved at 121° C. for 20 minutes. Ampicillin was added to this medium such that the final concentration reached 100 μg/mL, and one loopful of the resulting transformant strain No. 5 was then inoculated therein, and incubated at 37° C. and 130 rpm for approximately 20 hours. Only the cells were separated from the culture solution through centrifugation at 5,000 G for 15 minutes. Subsequently, the cells were resuspended in 50 mL of a physiological saline solution, and the wet cells were then obtained through recentrifugation. One hundred milligrams of the wet cells was suspended in 200 mL of a 50 mM potassium phosphate aqueous solution (pH 7.0), and 10 mL of acrylonitrile were added to this suspension. The mixture was reacted at 10° C. for 1 hour while being gently stirred. After the completion of the reaction, the reaction solution was analyzed through HPLC as in Example 1. Then, only acrylamide was present in the reaction solution, and acrylonitrile and acrylic acid were not observed therein. That is, the conversion and the selectivity were 100%.

EFFECTS OF THE INVENTION

The invention provides a nitrile hydratase activation protein participating in activation of nitrile hydratase derived from *Pseudonocardia thermophila* JCM3095, and a gene sequence encoding the same. Further, the invention provides a recombinant plasmid containing the gene, a recombinant plasmid containing the gene and a nitrile hydratase gene, a transformant strain obtained through transformation with the recombinant plasmid, and a process for producing a corresponding amide compound from a nitrile compound using the culture solution, the cells obtained by incubating the transformant strain, or treated products of the cells.

Moreover, according to the invention, in the industrial production of the amide compound from the nitrile compound using nitrile hydratase derived from *Pseudonocardia thermophila*, the enzyme can be expressed in a large amount by the genetic engineering method, whereby the production cost of the enzyme occupied in the production cost of the amide compound can be reduced.

What is claimed is:

1. An isolated and purified nucleotide sequence encoding a nitrile hydratase activation protein of SEQ ID NO: 1.

2. The isolated and purified nucleotide sequence from the $1328^{th}$ base to the $1762^{nd}$ base of SEQ ID NO:2.

3. A recombinant plasmid prepared by inserting the isolated and purified nucleotide sequence according to of claim 1, into a plasmid vector having a control region for expression of said sequence and a region for autonomous replication.

4. The recombinant plasmid of claim 3,
wherein the isolated and purified nucleotide sequence is the isolated and purified nucleotide sequence of claim 2.

5. The recombinant plasmid, containing the following (1) and (2) and capable of expressing an active nitrile hydratase derived from *Pseudonocardia thermophila* JCM3095, FERM BP-7379:

(1) an isolated and purified nucleotide sequence encoding α-subunit and β-subunit of the nitrile hydratase; and
(2) an isolated and purified nucleotide sequence encoding a protein participating in activation of nitrile hydratase derived from *Pseudonocardia thermophila* JCM3095; FERM BP-7379, wherein a control region for expression of (1) is different from a control region for expression of (2).

6. The recombinant plasmid, containing the following (1), (2) and (3), and capable of expressing an active nitrile hydratase derived from *Pseudonocardia thermophila* JCM3095, FERM BP-7379:

(1) an isolated and purified nucleotide sequence encoding α-subunit of the nitrile hydratase;
(2) an isolated and purified nucleotide sequence encoding β-subunit of the nitrile hydratase; and
(3) an isolated and purified nucleotide sequence encoding a protein participating in activation of nitrile hydratase-derived from *Pseudonocardia thermophila* JCM3095, FERM BP-7379, wherein a control region for expression of (1), a control region of expression of (2) and a control region for expression of (3) are different from one another.

7. The recombinant plasmid of claim 6,
wherein a control region for expression of (2) is different from a control region for expression of (1) and serves also as a control region for expression of (3).

8. The recombinant plasmid pPT-H1.

9. A microbial strain transformed with the recombinant plasmid of claim 3.

10. A microbial strain transformed with the recombinant plasmid of claim 4.

11. A microbial strain transformed with the recombinant plasmid of claim 5.

12. A microbial strain transformed with the recombinant plasmid of claim 6.

13. A microbial strain transformed with the recombinant plasmid of claim 7.

14. A microbial strain transformed with the recombinant plasmid of claim 8.

15. The recombinant plasmid pPT-G1.

16. A microbial strain transformed with the recombinant of claim 15.

* * * * *